US007365132B2

(12) United States Patent
Moody et al.

(10) Patent No.: US 7,365,132 B2
(45) Date of Patent: Apr. 29, 2008

(54) MONOMERS CONTAINING POLYOXYALKYLENES AND POLYMER SUPPORTS THEREFROM

(75) Inventors: David John Moody, Grangemouth (GB); Donald Alfred Wellings, Blackley (GB)

(73) Assignee: Avecia Biotechnology Inc., Milford, MA (US)

( * ) Notice: Subject to any disclaimer, the term of this patent is extended or adjusted under 35 U.S.C. 154(b) by 149 days.

(21) Appl. No.: 10/512,145

(22) PCT Filed: Apr. 25, 2003

(86) PCT No.: PCT/GB03/01774

§ 371 (c)(1),
(2), (4) Date: May 10, 2005

(87) PCT Pub. No.: WO03/091311

PCT Pub. Date: Nov. 6, 2003

(65) Prior Publication Data

US 2005/0256283 A1    Nov. 17, 2005

(30) Foreign Application Priority Data

Apr. 26, 2002  (GB) ................... 0209539.6

(51) Int. Cl.
*C08F 16/12* (2006.01)
*C07C 43/215* (2006.01)
(52) U.S. Cl. ................ 525/328.9; 526/292.9; 526/313; 526/333; 568/608; 568/616; 552/105
(58) Field of Classification Search ............... 568/608, 568/616; 526/333, 313, 292.9; 552/105; 525/328.9

See application file for complete search history.

(56) References Cited

U.S. PATENT DOCUMENTS

| RE28,212 E | * | 10/1974 | Grosjean .................. 528/345 |
| 4,814,514 A | * | 3/1989 | Yokota et al. ............. 568/608 |
| 4,908,405 A | | 3/1990 | Bayer et al. |
| 5,459,003 A | * | 10/1995 | Ota .......................... 568/680 |
| 5,466,758 A | | 11/1995 | Yoon-Sik et al. |
| 6,395,842 B1 | | 5/2002 | Main ......................... 525/384 |

FOREIGN PATENT DOCUMENTS

| WO | WO 97/27266 | 7/1997 |
| WO | WO 00/02953 | 1/2000 |
| WO | WO 01/26692 | 4/2004 |

OTHER PUBLICATIONS

Greene et al, Protective Groups in Organic Synthesis, Wiley-Interscience, 1999, pp. 17-23 and 102-105.*
Hiratani K. et al.: "Preparation and Catalytic Behaviour of Polymers with Pendant Oligoethyleneoxy-Groups (Polymers of Non-Cyclic Crown Ethers)" Israel Journal of Chemistry, XX,XX, vol. 18, No. ¾, 1979, pp. 208-213, XP000604342.
Harris, J.M., "Laboratory Synthesis of Polyethylene Glycol Derivatives", Journal of Macromolecular Science-Reviews in Macromolecular Chemistry, vol. C-25, No. 3, pp. 325-373 (Jan. 1, 1985).
Balakrishnan et al., "Particle Size Control in Suspension Copolymerization of Styrene, Chloromethylstyrene, and Divinylbenzene", Journal of Applied Polymer Science, 27:133-138 (1982).

* cited by examiner

*Primary Examiner*—Fred Teskin
(74) *Attorney, Agent, or Firm*—Morgan, Lewis & Bockius LLP

(57) ABSTRACT

A polymer support is provided which comprises protected hydroxypoly$C_{2-4}$ alkyleneoxy chains attached to a cross-linked polymer wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chains are protected with an acid labile group. The acid labile protecting group is preferably a poly-aryl methane protecting group. A monomer and process for the preparation of said support are also provided.

17 Claims, No Drawings

MONOMERS CONTAINING POLYOXYALKYLENES AND POLYMER SUPPORTS THEREFROM

The present invention relates to a process for the synthesis of polymers which are useful as supports in solid phase organic synthesis (SPOS) and to intermediates for use therein.

PCT/GB99/02193 discloses a series of novel polymer resin supports which find use as supports in solid phase organic synthesis (SPOS).

These polymer resins are of commercial importance and there exists a need for improved methods for their synthesis. We have found that certain novel monomers and resins find use in improved routes to these polymers.

According to a first aspect of the present invention there is provided a monomer which comprises a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an acid labile protecting group.

The hydroxypoly$C_{2-4}$ alkyleneoxy chains attached to the monomer according to the present invention are often selected from hydroxypolyethyleneoxy (HO(CH$_2$CH$_2$O)$_{2-10}$—), hydroxypolypropyleneoxy (HO(CH$_2$CH(CH$_3$)O)$_{2-10}$—) and hydroxypolybutyleneoxy (HO(CH$_2$CH(C$_2$H$_5$)O)$_{2-10}$—) chains. In a preferred embodiment of the invention the hydroxypoly$C_{2-4}$ alkyleneoxy chain is hydroxypolyethyleneoxy.

The number of $C_{2-4}$ alkyleneoxy groups in the hydroxypoly$C_{2-4}$ alkyleneoxy chain can range from 2 to 10, but is preferably from 2 to 8 and more preferably from 3 to 5. Most preferably, there are four $C_{2-4}$ alkyleneoxy groups in the hydroxypoly$C_{2-4}$ alkyleneoxy chain.

In a highly preferred embodiment of the invention the hydroxypoly$C_{2-4}$ alkyleneoxy chain is hydroxytetraethyleneoxy (HO(CH$_2$CH$_2$O)$_4$—).

The polymerisable unit of the monomer according to the present invention is often selected from optionally substituted styrenes, acrylates and acrylamides. In a preferred embodiment of the invention the polymerisable unit is an optionally substituted styrene, optionally substituted methylstyrene, optionally substituted ethyl (meth)acrylate, optionally substituted propyl (meth)acrylate or optionally substituted N-methyl (meth)acrylamide.

In a highly preferred embodiment of the invention the polymerisable unit is an optionally substituted styrene or optionally substituted methylstyrene.

When the polymerisable unit is an optionally substituted styrene or optionally substituted methylstyrene, the phenyl ring of the styrene is preferably optionally substituted by 1 or 2 substituents often selected from methyl, ethyl, propyl, fluoro, chloro and bromo.

When the polymerisable unit is an optionally substituted styrene or optionally substituted methylstyrene, preferably the protected hydroxypoly$C_{2-4}$ alkyleneoxy chain is attached to an optionally substituted styrene or optionally substituted methylstyrene via an oxygen atom directly attached to the phenyl ring of the optionally substituted styrene or optionally substituted methylstyrene.

Acid labile protecting groups are groups which are labile under acid conditions. Acid labile protecting groups include poly-aryl methane protecting groups.

Poly-aryl methane protecting groups include optionally substituted di-aryl methanes and optionally substituted tri-aryl methanes. Optional substituents may reside on one or more of the aryl groups, and each aryl group may carry one or more substituents. Di-aryl methanes may also be optionally substituted on the carbon to which the two aryls are attached, preferably the optional substituent is an alkyl group.

Aryl refers to aryl groups which may contain 1 ring or 2 or more fused rings, the fused rings optionally may include cycloalkyl, aryl or heterocyclic rings. Examples of aryl groups include phenyl, tolyl, fluorophenyl, chlorophenyl, bromophenyl, trifluoromethylphenyl, anisyl, naphthyl xanthyl, pyridyl, pyrimidyl, thiophenyl, furanyl, indolyl, quinolyl and isoquinolyl groups.

Preferred aryl groups are optionally substituted phenyl, optionally substituted naphthyl, and optionally substituted xanthyl groups.

Alkyl groups which may substitute the carbon of a di-aryl methane include linear and branched alkyl groups comprising up to 20 carbon atoms, particularly from 1 to 7 carbon atoms, preferably from 1 to 5 carbon atoms, most preferably 1 or 2 carbon atoms. Examples include methyl, ethyl, propyl, and iso-propyl groups.

When the poly-aryl methane is substituted, the substituent(s) should be such so as not to adversely affect the stability of the protecting group or the ability to remove the protecting group under acid conditions. Optional substituents include halogen, cyano, nitro, hydrocarbyl, amino, thiol, acyl, hydrocarbyl, perhalogentated hydrocarbyl, heterocyclyl, hydrocarbyloxy, poly(oxyalkylene)oxy, mono or di-hydrocarbylamino, hydrocarbylthio, esters, carbonates, amides, sulphonyl and sulphonamido groups wherein the hydrocarbyl groups are generally alkyl or aryl groups as defined above. One or more substituents may be present.

Examples of poly-aryl methane protecting groups include diphenylmethyl, naphthyldiphenylmethyl, phenylxanthyl [pixyl], triphenylmethyl [trityl], di-methoxyphenylphenylmethyl [dimethoxy trityl], methoxyphenyl-di-phenylmethyl [monomethoxy trityl], and 2-chlorophenyldi-phenylmethyl [2-chlorotrityl] groups In a preferred embodiment of the invention, the monomer is a compound of formula (1)

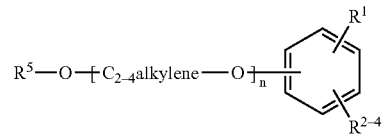

wherein
$R^1$ is an optionally substituted ethylene group;
$R^{2-4}$ are independently hydrogen, hydrocarbyl, halogen, or hydrocarbyloxy;
$R^5$ is an acid labile protecting group; and
n is 2 to 10.

Preferably, the acid labile protecting group is a poly-aryl methane protecting group. More preferably $R^5$ is a poly-aryl methane protecting group of formula:

—$CR^6R^7R^8$ wherein:
$R^6$ is hydrogen, optionally substituted alkyl or optionally substituted aryl group; and
$R^7$ and $R^8$ are each independently optionally substituted aryl groups, or $R^7$ & $R^8$ are optionally substituted aryl groups which may be linked to form an optionally substituted ring.

Alkyl groups which may be represented by $R^6$ include linear and branched alkyl groups comprising up to 20 carbon atoms, particularly from 1 to 7 carbon atoms, preferably from 1 to 5 carbon atoms, most preferably 1 or 2 carbon atoms. Examples include methyl, ethyl, propyl, and iso-propyl.

Aryl groups which may be represented by $R^6$, $R^7$ and $R^8$ may contain 1 ring or 2 or more fused rings, the fused rings optionally may include cycloalkyl, aryl or heterocyclic rings. Examples of aryl groups include phenyl, tolyl, fluorophenyl, chlorophenyl, bromophenyl, trifluoromethylphenyl, anisyl, naphthyl, pyridyl, pyrimidyl, thiophenyl, furanyl, indolyl, quinolyl and isoquinolyl groups.

Preferred aryl groups are optionally substituted phenyl.

When $R^7$ & $R^8$ are optionally substituted aryl groups which are linked in such a way that when taken together with the carbon atom to which they are attached that a ring is formed, it is preferred that the ring is a 5, 6 or 7 membered ring. Examples where $R^7$ & $R^8$ are optionally substituted aryl groups which are linked to form an optionally substituted ring include xanthyl groups.

When any of $R^6$, R7 or $R^8$ is a substituted alkyl or substituted aryl group, the substituent(s) should be such so as not to adversely affect the stability of the protecting group or the ability to remove the protecting group under acid conditions. Optional substituents include halogen, cyano, nitro, hydrocarbyl, amino, thiol, acyl, hydrocarbyl, perhalogentated hydrocarbyl, heterocyclyl, hydrocarbyloxy, poly(oxyalkylene)oxy, mono or di-hydrocarbylamino, hydrocarbylthio, esters, carbonates, amides, sulphonyl and sulphonamido groups wherein the hydrocarbyl groups are generally alkyl, aryl, alkaryl and aralkyl groups, the alkyl and aryl groups are as defined above. One or more substituents may be present.

Most preferably, $R^5$ is a poly-aryl methane protecting group of formula:

wherein:

$R^6$ is an optionally substituted aryl group; and $R^7$ and $R^8$ are each independently optionally substituted aryl groups, or $R^7$ & $R^8$ are optionally substituted aryl groups which may be linked to form an optionally substituted ring.

In a highly preferred embodiment of the present invention, the acid labile protecting group is an optionally substituted trityl group.

According to a second aspect of the present invention there is provided a monomer which comprises a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an optionally substituted trityl group.

Optionally substituted trityl groups include triphenylmethyl [trityl], di-methoxyphenylphenylmethyl [dimethoxy trityl], methoxyphenyl-di-phenylmethyl [monomethoxy trityl], and 2-chlorophenyidi-phenylmethyl [2-chlorotrityl] groups.

In a most preferred embodiment of the present invention, the monomer is a compound of formula (1a)

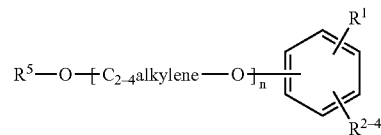

wherein $R^1$ is an optionally substituted ethylene group;

$R^{2-4}$ are independently hydrogen, hydrocarbyl, halogen, or hydrocarbyloxy;

$R^5$ is an optionally substituted trityl group; and n is 2 to 10.

Preferably, $R^1$ is a CH=$CH_2$, CH=$CHCH_3$, or C($CH_3$)=$CH_2$ group. Most preferably, $R^1$ is a CH=$CH_2$.

Preferably, the $R^5$O—[—$C_{2-4}$ alkylene-O—]$_n$ group is para to $R^1$.

Preferably, [—$C_{2-4}$ alkylene-O—]$_n$ is [—$CH_2CH_2O$—]$_n$, [—$CH_2CH(CH_3)O$—]$_n$, [—$CH_2CH_2CH_2CH_2O$—]$_n$ or [—$CH_2CH(C_2HS)O$—]$_n$, and most preferably [—$CH_2CH_2O$—]$_n$.

Preferably n is 2 to 8, more preferably n is 3 to 5. Most preferably n is 4.

Preferably $R^{2-4}$ are all hydrogen.

Hydrocarbyl includes alkyl, aryl, alkaryl and aralkyl groups. Preferably when any of $R^{2-4}$ are hydrocarbyl or hydrocarbyloxy groups the hydrocarbyl is an alkyl group, most preferably a $C_{1-4}$alkyl group.

The monomers according to the first and second aspects of the present invention are useful in polymerisation reactions to form resins from which the polymer supports disclosed in PCT/GB99/02193 can be obtained.

Accordingly, a third aspect of the present invention provides a process for the preparation of a polymer support comprising polymerisation of a monomer comprising a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an acid labile protecting group, under conditions to produce cross-linking.

The monomer comprising a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an acid labile protecting group can be as described above in the first and second aspects of the present invention.

Preferably the acid labile protecting group is a poly-aryl methane protecting group, more preferably an optionally substituted trityl group. The preferred poly-aryl methane protecting groups and the optionally substituted trityl groups are as defined above in the first and second aspects of the present invention.

Optionally, in the process of the present invention the monomer comprising a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an acid labile protecting group, preferably an optionally substituted tritly group, may comprise a mixture of isomers.

Preferably, when a mixture of isomers is used in the process of the present invention, the monomer is a compound of formula (1) or (1a). Most preferably, the monomer is a mixture of isomers wherein $R^5O—[—C_{2-4}$ alkylene-$O—]_n$ group and $R^1$ occupy isomeric positions on the phenyl ring.

Preferably, in the process of the present invention, the monomer comprising a protected hydroxypoly$C_{2-4}$ alkyleneoxy chain attached to a polymerisable unit is co-polymerised in the presence of a cross linking monomer.

The extent of cross linking in the polymers is determined by the concentration of cross linking monomer in the polymerisation reaction. Generally the weight % of crosslinking monomer is in the range of from 0.1 to 70%, commonly from 0.5 to 20%, such as from 1 to 10%, and most preferably no more than 5% by weight. Polymers comprising no more than 20% by weight of cross-linking monomer are generally swellable, whilst polymers comprising greater than 20% of crosslinking monomer are generally not swellable.

Suitable cross-linking monomers include divinyl benzene (DVB) or multifunctional (meth)acrylates such as di/tri acrylates or di/tri methacrylates such as ethylene glycol diacrylate, ethylene glycol dimethacrylate, trimethylopropane trimethacrylate, trivinylbenzene or N,N'-bis-acryloyl ethylene diamine. Preferably the cross-linking monomer is DVB.

Preferably 0.5 to 5% by weight of DVB is used. Most preferably 1 to 3% by weight DVB is used.

In one aspect of the present invention a level of at least 5% crosslinking monomer is used in conjunction with compounds miscible with the organic phase which can act as pore-forming agents or porogens. Typical porogens can include, but are not limited to, organic compounds which are good solvents for the polymer, such as organic aromatic hydrocarbons, chlorinated aliphatic or aromatic hydrocarbons and cyclic aliphatic ethers, organic compounds which are poor solvents for the resulting polymer, such as aliphatic alcohols, ketones, aliphatic hydrocarbons, aliphatic carboxylic acids and linear polymers. Preferably porogens are selected from toluene, xylene, chlorobenzene, tetrahydrofuran, dioxane, 2-ethyl-1-hexanol, 2-octanol, 1-decanol, 1-dodecanol, acetone, butanone, n-heptane, n-decane, 1-decanoic acid and linear polystyrene of molecular weight 500 to 5000000 g/mol. The resulting polymers have substantially non-swelling behaviour and generally possess a meso- to macro-porous nature, by which mode reagents can access the polymer-bound functionality.

Optionally, in the process of the present invention, the monomer comprising a protected hydroxypoly$C_{2-4}$ alkyleneoxy chain attached to a polymerisable unit is co-polymerised in the presence of one or more monomers selected from styrenes, for example styrene, hydroxystyrene, methoxystyrene, methylstyrene, hydroxymethylstyrene and chloromethylstyrene, esters of acrylic acid and esters of (meth) acrylic acid, for example methyl acrylate, ethyl acrylate, methyl methacrylate, ethyl acrylate, hydroxyethyl (meth) acrylate and hydroxypropyl (meth)acrylate, and acrylamides, for example N-methyl acrylamide and N-methylol (meth)acrylamide; wherein the phenyl ring in the styrenes is optionally substituted by 1 or 2 substituents often selected from methyl, ethyl, propyl, fluoro, chloro and bromo and wherein hydroxy groups, especially phenolic hydroxy groups, which may be present in the monomers are optionally protected and may subsequently be deprotected.

In a preferred process of the present invention, the monomer comprising a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an optionally substituted trityl group is co-polymerised in the presence of one or more cross linking monomers, and one or more monomers selected from styrenes, esters of acrylic acid and esters of (meth)acrylic acid, or acrylamides.

In a highly preferred process of the present invention, the monomer comprising a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an optionally substituted trityl group is co-polymerised in the presence of DVB and styrene.

When the polymer support is produced by polymerisiation of a mixture of monomers comprising the monomer comprising a protected hydroxypoly$C_{2-4}$ alkyleneoxy chain attached to a polymerisable unit wherein the protected hydroxypoly$C_{2-4}$ alkyleneoxy chain contains from 2 to 10 $C_{2-4}$ alkyleneoxy groups and wherein the hydroxypoly$C_{2-4}$ alkyleneoxy chain is protected with an acid labile protecting group, preferably an optionally substituted trityl group, and one or more monomers selected from styrenes, esters of acrylic acid and esters of (meth)acrylic acid, or acrylamides, the weight percentage of the monomer comprising a protected hydroxypoly$C_{2-4}$ alkyleneoxy chain attached to a polymerisable unit of the total weight of the monomers present is preferably in the range of from 1-99%, more preferably in the range of from 5-80% and most preferably from 15% to 70%.

The process of the present invention is preferably carried out by aqueous suspension polymerisation. The monomers are suspended as droplets (1-1000 μm) in water. Stabilisers are usually added to prevent agglomeration of the droplets, for example polyvinyl alcohol, polyacrylic acid, polyvinyl pyrrolidone, polyalkylene oxide, derivatives of cellulose, such as hydroxypropylmethylcellulose or ethylcellulose, barium sulphate, magnesium sulphate or sodium sulphate. The suspension is also normally stirred to maintain the suspension.

Optionally, organic non-water miscible solvents may be used in the polymerisation process. Organic non-water miscible solvents may assist droplet formation in aqueous suspension polymerisation, or may act as porogens.

Optionally inorganic salts may be added to the aqueous phase in aqueous suspension polymerisation. Inorganic salts may assist droplet formation by suppressing monomer solubility in the aqueous medium.

A free radical initiator is preferably used to initiate polymerisation. The type of initiator will generally be selected based on the monomers used. Examples of preferred free radical initiators include benzoyl peroxide, dioctanoyl peroxide, lauroyl peroxide, 2,2'-azobisisobutyronitrile and 2,2'-azobis(2,4-dimethylvaleronitrile).

Polymerisation is typically assisted by heating the mixture in the range of 15° C. to 160° C., preferably 50° C. to 90° C. It will be recognised that the temperature to which the mixture can be heated depends upon the type of monomer and initiator employed.

The resultant polymer may then be washed with suitable solvents such as tetrahydrofuran, methanol and water, dried and bead size classified, for example, by sieving.

Accordingly a further aspect of the present invention provides a polymer support which comprises protected hydroxypoly$C_{2-4}$ alkyleneoxy chains attached to a cross-linked polymer wherein the protected hydroxypoly$C_{2-4}$ alkyleneoxy chain contains from 2 to 10 $C_{2-4}$ alkyleneoxy groups and wherein the hydroxypolyC$_{2-4}$ alkyleneoxy chains are protected with an acid labile protecting group, preferably an optionally substituted trityl group.

The protected hydroxypolyC$_{2-4}$ alkyleneoxy chains attached to a cross-linked polymer according to the present invention are often selected from protected hydroxypolyethyleneoxy (protected HO(CH$_2$CH$_2$O)$_{2-10}$—), protected hydroxypolypropyleneoxy (protected HO(CH$_2$CH(CH$_3$)O)$_{2-10}$—) and protected hydroxypolybutyleneoxy (protected HO(CH$_2$CH(C$_2$H$_5$)O)$_{2-10}$—) chains. In a preferred embodiment of the invention the protected hydroxypolyC$_{2-4}$ alkyleneoxy chain is protected hydroxypolyethyleneoxy.

The number of C$_{2-4}$ alkyleneoxy groups in the protected hydroxypolyC$_{2-4}$ alkyleneoxy chain can range from 2 to 10, but is preferably from 2 to 8 and more preferably from 3 to 5. Most preferably, there are four C$_{2-4}$ alkyleneoxy groups in the protected hydroxypolyC$_{2-4}$ alkyleneoxy chain.

In a highly preferred embodiment of the invention the protected hydroxypolyC$_{2-4}$ alkyleneoxy chain is protected hydroxytetraethyleneoxy (protected HO(CH$_2$CH$_2$O)$_4$—)—.

Preferably the protected hydroxypolyC$_{2-4}$ alkyleneoxy chains are attached to a cross-linked polymer via phenoxy ether linkages.

The invention, in its broadest aspect, relates to the particular polymer supports however prepared.

Preferably, the polymer support of the present invention is obtainable by the process of the third aspect of the present invention.

The acid labile protecting groups may subsequently be removed to give the cross-linked polymer containing free hydroxy groups.

Methods appropriate for removal of the optionally substituted trityl group include, for example, acid-hydrolysis. Commonly a mixture of trifluoroacetic acid in methylene chloride can be employed. The reader is referred to Advanced Organic Chemistry, 4$^{th}$ Edition, by Jerry March, published by John Wiley & Sons 1992, for general guidance on reaction conditions and reagents.

Where appropriate, other methods may be also used for the removal of the acid labile protecting groups, for example the use of iodine under neutral conditions may be used to remove trityl groups, and photolysis may be used to remove pixyl groups.

Preferably, when the protecting groups are removed the resulting polymer support has from about 0.1 to about 5 meq free hydroxy groups per gram of polymer.

Cross-linked polymers containing a free hydroxy group are usually produced as beads which range in size from 10 μm to 2000 μm. Preferably the bead size is from 50 μm to 1000 μm and most preferably from 75 μm to 500 μm. The cross-linked polymer beads are generally produced by an aqueous suspension polymerisation process, for example see Journal of Applied Polymer Science, 1982, 27, 133-138, incorporated herein by reference.

The polymer support obtained when the protecting groups are removed from the support according to the present invention has a hydroxy functionality of from 0.1 to about 5, for example up to 4.8 meq (milliequivalents) of hydroxy per gram of polymer, and often from 0.5 to. 3.5, commonly 1.0 to 3.3 meq per gram for example from 1.5 to 3 meq per gram of polymer. In many embodiments, the polymer support obtained when the protecting groups are removed have from 0.5 to 2 meq of hydroxy per gram of polymer.

The polymer supports described above of use in solid phase organic synthesis, accordingly there is provided the use of a polymer support which comprises protected hydroxypolyC$_{2-4}$ alkyleneoxy chains attached to a cross-linked polymer wherein the protected hydroxypolyC$_{2-4}$ alkyleneoxy chain contains from 2 to 10 C$_{2-4}$ alkyleneoxy groups and wherein the hydroxypolyC$_{2-4}$ alkyleneoxy chains are protected with an acid labile group in solid phase organic synthesis.

Preferably, the polymer support is obtained by the process of third aspect of the present invention.

Preferably, the polymer support is deprotected prior to use.

The invention will now be described, without limitation, by the following examples in which, unless otherwise stated:— a) FT-IR spectra were obtained using swollen gels in dichloromethane held between sodium chloride plates, and an ATI Genesis (Matteson)spectrometer.

b) $^{13}$C magic angle (MAS) NMR spectra were obtained using solvent swollen gels in the rotor of a Bruker MAS probe on a 400 MHz NMR spectrometer.

c) yields are given for illustration and are not necessarily the maximum attainable.

d) the following abbreviations have been used: THF=tetrahydrofuran, DMF=N,N-dimethylformamide, FMOC=fluorenylmethoxycarbonyl, PEG=polyethyleneglycol and THP=tetrahydropyranyl.

EXAMPLES

Example 1

Preparation of Trityl-tetraethyleneglycoxystyrene

Stage 1

Tetraethyleneglycol (174 g, 0.9 mol) was placed in a 3 necked round bottom flask fitted with a thermometer and reflux condenser. Pyridine (11 cm$^3$, 0.135 mol) was added to the mixture stirred. Triphenylmethylchloride (25 g, 0.09 mol) was dissolved in toluene (30 cm$^3$) and this solution was added slowly to the mixture. The mixture was heated to 50° C. and the temperature maintained for 1 h.

The mixture was allowed to cool and toluene (200 cm$^3$) was added to the flask. The solution was extracted with water (500 cm$^3$). The aqueous phase was back extracted with toluene (2×100 cm$^3$). The organic layers were combined and washed with water (2×100 cm$^3$), dried over MgSO$_4$ and filtered. The toluene was removed by evaporation under reduced pressure to yield a pale yellow oil (yield 38.5 g, 98% based on trityl).

Stage 2

Mono(trityl)tetraethyleneglycol (30 g, 0.069 mol), 4-toluenesulfonyl chloride (14.4 g, 0.076 mol) and dry tetrahydrofuran (50 cm$^3$) were placed in a 3 necked round bottom flask fitted with a thermometer and reflux condenser. The flask was placed in a dry-ice bath and the mixture allowed to cool to ~−20° C. A solution of KOH (25.2 g, 0.45 mol) in water (100 cm$^3$) was added drop-wise over a period of 1 h whilst maintaining the temperature at <0° C. Following the addition the reaction mixture was stirred for 1 h whilst allowing the solution to warm to ambient.

The solution was extracted with diethylether (3×150 cm$^3$). The ether layer was dried over MgSO$_4$, filtered and evaporated under reduced pressure. The solid was washed with MeOH and dried under vacuum (yield 34.3 g, 85%).

Stage 3

NaOMe (0.55 g, 10.2 mmol) was dissolved in the minimum amount of N,N-dimethylformamide (DMF) and added to 4-acetoxystyrene (1.3 cm³, 8.5 mmol) contained in a round bottom flask. This solution was stirred at ambient for 45 min then a solution of the tosyl derivative of mono(trityl) tetraethyleneglycol (5 g, 8.5 mmol) in DMF was added. The reaction was allowed to continue overnight at ambient.

The DMF was removed by evaporation under reduced pressure. The oil remaining was dissolved in isopropylacetate and extracted with water. The organic layers were combined, dried over MgSO₄ and filtered. The solvent was removed by evaporation under reduced pressure to leave a pale yellow oil that crystallised on standing (yield 3.5 g, 77%).

Example 2

10 Litre Scale Preparation of Trityl-tetraethyleneglycoxystyrene

Stage 1

Tetraethylene glycol (4188 g, 21.5 mol) was added under a nitrogen atmosphere to a 10 l vessel equipped with a mechanical stirrer and stirred at 60 rpm. Pyridine (544 g, 6.9 mol) was added to the vessel and the mixture heated to 50° C. Triphenylmethyl chloride (1000 g, 3.6 mol) was dissolved in toluene (3000 ml) under N₂ atmosphere and added slowly to the glycol keeping the temperature below 60° C. The temperature was held at 50° C. for 2 hours and then cooled to room temperature. 2 l of toluene were added and the mixture extracted with 6 l of deionised water, the water phase extracted with 5 l of toluene. The combined organic extracts were washed with 2×4 l of DI water, dried over 500 g sodium sulphate and solvent removed under reduced pressure to yield 1230 g (74% based on trityl) of a pale yellow oil, 94.3% purity (by NMR)

Stage 2

Mono(trityl)tetraethyleneglycol (1766.4 g, 3.8 mol) was added to a 10 l vessel together with 3 l THF and cooled under agitation to −12° C. p-Toluenesulphonyl chloride (945 g, 5 mol) was added to the glycol/THF mixture. A solution of KOH (880 g, 15.7 mol) in deionised water (3 l) was added to the solution over 1 hour keeping the temp below −5° C. After completion of the addition the vessel was warmed to 25° C. and held for 12 hours. The phases were separated and the lower aqueous layer washed with 2×2.5 L THF, the organic layers combined and solvent removed under reduced pressure. The orange/brown oil in 7.5 l isopropyl acetate was extracted with 10 l water and then 5×2 l water, dried over magnesium sulphate (500 g) and solvent removed to give 1837 g (78.0%) of the product as a viscous orange oil, purity 95.3% (by NMR).

Stage 3

Deoinised water (1.5 l) and THF (2.1 l) were added to a 10 L vessel and agitation started at 100 rpm. The vessel was cooled down to −12° C. and potassium hydroxide (535 g, 9.5 mol) was added slowly. Acetoxystyrene (575 ml, 3.7 mol) in THF (1 l), was added to the vessel over about 30 minutes with cooling. The vessel was heated to 30° C. and held for 1 hr, then cooled to 20° C. The Stage 2 product (1800 g, 2.9. mol) in 1050 ml THF was added to reaction vessel over 15 mins, then the mixture heated at 60° C. for 40 hrs. The reaction was cooled, the phases separated and the organic layers washed with 2×2 l of 8M aqueous potassium hydroxide. The solvent was removed under reduced pressure and the residue dissolved in toluene (5 l), washed with 3×2 l deionised water, then 2×2 l 1M aqueous sodium hydroxide, and finally 2×3 l DI water. The organic layer was dried with sodium sulphate (500 g) and solvent removed under reduced pressure to yield 1471 g (75%) of the product as an orange oil, purity 79.7% by NMR.

Example 3

Synthesis of Polymer and Subsequent Deprotection

Partially hydrolysed poly(vinyl alcohol) (Airvol 540, 34.9 g of 2.5 wt-% aqueous solution) and sodium chloride (31.2 g) were charged into a 2 l cylindrical baffled reactor containing deionised water (1181 ml) and equipped with a mechanical stirrer. A mixture of Stage 3 product (79.7%, 87.2 g), styrene (59.1 g), divinylbenzene (80%, 1.4 g) and lauroyl peroxide (5.2 g) were charged to the reactor and agitated at 400 rpm. After 20 minutes the stirrer speed was reduced to 300 rpm and the reaction heated with a water bath to 80° C. over 50 minutes. After 16 h, the reaction mixture was cooled, transferred to a 50 μm filter cloth bag and washed with deionised water (5×1 l). The polymer beads were then washed with THF (4×1 l) and dichloromethane (2×1 l) and stirred at room temperature under nitrogen in a 5 l flange flask/overhead stirrer with a mixture of dichloromethane (1800 ml), trifluoroacetic acid (128 g) and triethylsilane (51.5 g) for 4 hours. The product was then washed with dichloromethane (4×1 l) and hexane (5×1 l) before drying to constant weight in a vacuum oven, yielding 78 g of white polymer beads with a hydroxyl loading of 0.97 mmol/g.

The invention claimed is:

1. A monomer which comprises a protected hydroxypolyC₂₋₄ alkyleneoxy chain attached to a polymerisable unit capable of free radical polymerization wherein the protected hydroxypolyC₂₋₄ alkyleneoxy chain contains from 2 to 10 C₂₋₄ alkyleneoxy groups and wherein the hydroxypolyC₂₋₄ alkyleneoxy chain is protected with a poly-aryl methane protecting group.

2. A monomer of formula (1)

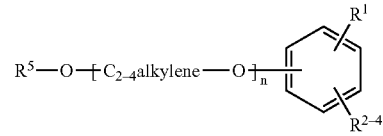

wherein
   $R^1$ is an optionally substituted ethylene group;
   $R^{2-4}$ are independently hydrogen, hydrocarbyl, halogen, or hydrocarbyloxy;
   $R^5$ is a poly-aryl methane protecting group; and
   n is 2 to 10.

3. A monomer according to claim 2 wherein $R^1$ is a CH═CH₂, CH═CHCH₃, or C(CH₃)═CH₂ group.

4. A monomer according to any of claims 2 or 3 wherein [—C₂₋₄alkylene-O—]ₙ is [—CH₂CH₂O—]ₙ, [—CH₂CH(CH₃)O—]ₙ, [—CH₂CH₂CH₂CH₂O—]ₙ or [—CH₂CH(C₂H₅)O—]ₙ.

5. A monomer according to claim 2 wherein $R^{2-4}$ are hydrogen.

6. A monomer according to claim 2 wherein $R^5$ is a poly-aryl methane protecting group of formula:

—CR⁶R⁷R⁸ wherein:

R$^6$ is hydrogen, optionally substituted alkyl or optionally substituted aryl group; and R$^7$ and R$^8$ are each independently optionally substituted aryl groups, or R$^7$ & R$^8$ are optionally substituted aryl groups which may be linked to form an optionally substituted ring.

7. A monomer according to claim 1 wherein the poly-aryl methane protecting group is an optionally substituted trityl group.

8. A process for the preparation of a polymer support comprising free radical polymerisation of a monomer comprising a protected hydroxypolyC$_{2-4}$ alkyleneoxy chain attached to a polymerisable unit wherein the protected hydroxypolyC$_{2-4}$ alkyleneoxy chain contains from 2 to 10 C$_{2-4}$ alkyleneoxy groups and wherein the hydroxypolyC$_{2-4}$ alkyleneoxy chain is protected with a poly-aryl methane protecting group, under conditions to produce cross-linking.

9. A process according to claim 8 wherein the monomer comprising a protected hydroxypolyC$_{2-4}$ alkyleneoxy chain attached to a polymerisable unit is copolymerised in the presence of one or more one or more monomers selected from the group consisting of styrenes, esters of acrylic acid and esters of (meth)acrylic acid, and acrylamides.

10. A process according to claim 8 wherein the monomer comprising a protected hydroxypolyC$_{2-4}$ alkyleneoxy chain attached to a polymerisable unit is copolymerised in the presence of one, or more cross linking monomers, and one or more monomers selected from the group consisting of styrenes, esters of acrylic acid and esters of (meth)acrylic acid, and acrylamides.

11. A process according to claim 8 wherein the monomer comprising a protected hydroxypolyC$_{2-4}$ alkyleneoxy chain attached to a polymerisable unit is copolymerised in the presence of divinyl benzene, and styrene.

12. A process according to claim 8 wherein the monomer comprising a protected hydroxypolyC$_{2-4}$ alkyleneoxy chain attached to a polymerisable unit is a monomer of formula (1)

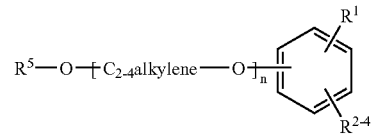

wherein
R$^1$ is an optionally substituted ethylene group;
R$^{2-4}$ are independently hydrogen, hydrocarbyl, halogen, or hydrocarbyloxy;
R$^5$ is a poly-aryl methane protecting group; and
n is 2 to 10.

13. A polymer support which comprises protected hydroxypolyC$_{2-4}$ alkyleneoxy chains attached to a cross-linked polymer obtained by free radical polymerization wherein the protected hydroxypolyC$_{2-4}$ alkyleneoxy chain contains from 2 to 10 C$_{2-4}$ alkyleneoxy groups and wherein the hydroxypolyC$_{2-4}$ alkyleneoxy chains are protected with a poly-aryl methane protecting group.

14. A polymer support according to claim 13 wherein the poly-aryl methane protecting group is an optionally substituted trityl group.

15. A polymer support obtained by the process of claim 8.

16. A process for solid phase organic synthesis which comprises deprotecting a protected solid support, and performing solid phase organic synthesis on the deprotected solid support, wherein the protected solid support is a polymer support according to claim 13.

17. A process according to claim 9, wherein the monomer comprising a protected hydroxypolyC$_{2-4}$ alkyleneoxy chain attached to a polymerizable unit is copolymerized in the presence of one or more monomers selected from the group consisting of styrene, hydroxystyrene, methoxystyrene, methyistyrene, hydroxymethylstyrene, chloromethyl styrene, methyl acrylate, ethyl acrylate, methyl methacrylate, ethyl acrylate, hydroxyethyl(meth)acrylate, hydroxypropyl (meth)acrylate, N-methyl acrylamide and N-methylol(meth)acrylamide.

* * * * *